United States Patent [19]

Moffatt

[11] 3,998,807

[45] Dec. 21, 1976

[54] ARABINOFURANOSYL CYTOSINES AND METHODS OF MAKING

[75] Inventor: John G. Moffatt, Los Altos, Calif.

[73] Assignee: Syntex (U.S.A.) Inc., Palo Alto, Calif.

[22] Filed: Mar. 3, 1972

[21] Appl. No.: 231,754

[52] U.S. Cl. .................................. 536/23; 424/180
[51] Int. Cl.$^2$ ...................................... C07H 19/08
[58] Field of Search ............................ 260/211.5 R

[56] References Cited

UNITED STATES PATENTS

| 3,155,646 | 11/1964 | Hunter | 260/211.5 R |
|---|---|---|---|
| 3,208,997 | 9/1965 | Iwai et al. | 260/211.5 R |
| 3,328,388 | 6/1967 | Shen et al. | 260/211.5 R |
| 3,338,882 | 8/1967 | Wechter et al. | 260/211.5 R |
| 3,463,850 | 8/1969 | Shen et al. | 260/211.5 R |
| 3,658,788 | 4/1972 | Orgel et al. | 260/211.5 R |
| 3,709,874 | 1/1973 | Moffatt et al. | 260/211.5 R |
| 3,755,296 | 8/1973 | Kanai et al. | 260/211.5 R |
| 3,894,000 | 8/1975 | Wechter et al. | 260/211.5 R |

FOREIGN PATENTS OR APPLICATIONS

| 2,202,518 | 1972 | Germany | 260/211.5 R |

OTHER PUBLICATIONS

Montgomery et al., J. Medicinal Chem., vol. 15, No, 1, 1971, pp. 116–118.

Primary Examiner—Johnnie R. Brown
Attorney, Agent, or Firm—Lawrence S. Squires; William B. Walker

[57] ABSTRACT

3'-O-Acyl- and 3-'-O-acyl-5-'-O-acyl- derivatives of 1-($\beta$-D-arabinofuranosyl)-cytosines and methods of preparing these compounds and also $O^2$,2'-anhydro-1-(3'-O-acyl-5'-O-acyl-$\beta$-D-arabinofuranosyl)-cytosine salts. The $O^2$,2'-anhydro-1-(3'-O-acyl-5'-O-acyl-$\beta$-D-arabinofuranosyl)-cytosine nucleoside salts are prepared by direct acid catalyzed acylation of the salts of the corresponding $O^2$,2'-anhydro-1-($\beta$-D-arabinofuranosyl)-cytosines or 3'-O-acyl- derivatives, under carefully controlled conditions. The 3'-O-acyl- and 3'-O-acyl-5'-O-acyl-1-($\beta$-D-arabinofuranosyl)-cytosines are prepared from the corresponding $O^2$,2'-anhydro nucleosides via selective cleavage of the $O^2$,2'-anhydro bridge under carefully controlled conditions. The compounds exhibit anti-viral, cytotoxic and anti-neoplastic activity, and thus are useful for the treatment of mammals where such agents are indicated.

13 Claims, No Drawings

ARABINOFURANOSYL CYTOSINES AND METHODS OF MAKING

BACKGROUND OF THE INVENTION

1. Field of the Invention

This invention relates to $O^2,2'$-anhydro-1-($\beta$-D-arabinofuranosyl)-cytosine nucleosides and 1-($\beta$-D-arabinofuranosyl)-cytosine nucleosides and salts thereof and to methods of preparing such nucleosides and salts. In a further aspect this invention relates to methods of preparing salts of $O^2,2'$-anhydro-1-(3'-O-acyl-5'-O-acyl-$\beta$-D-arabinofuranosyl)-cytosine nucleosides. In a still further aspect this invention relates to 3'-O-acyl- and 3'-O-acyl-5'-O-acyl- derivatives of 1-($\beta$-D-arabinofuranosyl)-cytosine nucleosides and salts thereof and methods of preparing such compounds and salts.

2. The Prior Art

The salts of $O^2,2'$-anhydro-1-($\beta$-D-arabinofuranosyl)-cytosine and its 5-halo, 5-lower alkyl and 5-halo(alkyl)cytosine derivatives are known to the art (note, for example, Walwick et al. Proc. Chem. Soc., 84 (1959) and U.S. Pat. No. 3,463,850). However, because of the instability under even mild basic conditions of the parent compounds, and also the great insolubility of the salts in most inert organic solvents, these salts cannot be acylated at the 3'-position by conventional nucleoside acylation procedures. For example, treatment of the salts of $O^2,2'$-anhydro-1-($\beta$-D-arabinofuranosyl)-cytosine and their derivatives, with even such mild bases as pyridine or aqueous pyridine or aqueous sodium bicarbonatecarbonate buffer, causes neutralization of the salt to give the unstable free base which decomposes with cleavage of the $O^2,2'$-anhydro linkage. Also attempted acylation with acyl anhydrides in pyridine results in extensive decomposition. Accordingly, I have now discovered a process for preparing the salts of $O^2,2'$-anhydro-1-(3',5'-di-O-acyl-$\beta$-D-arabinofuranosyl)-cytosine(s) directly from the salts of the corresponding $O^2,2'$-anhydro-1-($\beta$-D-arabinofuranosyl)-cytosines and 3'-O-acyl- derivatives thereof.

Similarly with respect to the 3',5'-di-O-acyl- derivatives, and particularly the 3'-O-acyl- derivatives of 1-($\beta$-D-arabinofuranosyl)-cytosines, these compounds could not be pragmatically made by conventional procedures. Here the problem is not one of stability, since the parent compounds are stable, but rather one of selectivity, since invariably conventional acylation procedures would result in preferential acylation of the more reactive free hydroxy at the 5'-position of the sugar moiety.

Thus selective acylation of the 5'-hydroxyl group of 1-($\beta$-D-arabinofuranosyl)-cytosine is quite feasible due to the greater reactivity of the primary hydroxy group relative to the secondary 2'- or 3'-hydroxyl functions. It is also presumably possible to obtain 1-(2',3'-di-O-acyl-$\beta$-D-arabinofuranosyl)-cytosine via initial blocking of the more reactive 5'-hydroxyl group with an acid labile substituent such as the trityl group (see e.g., J. Med. Chem., 10, 762 (1967) for the preparation of 1-(5'-O-trityl-$\beta$-D-arabinofuranosyl)-cytosine). There is, however, no apparent difference in reactivity between the 2'- and 3'-hydroxyl groups of arabinofuranosyl nucleosides and accordingly there is no selective way for preparing either 1-(3'-O-acyl-$\beta$-D-arabinofuranosyl)-cytosines or 1-(3',5'-di-O-acyl-$\beta$-D-arabinofuranosyl)-cytosines containing unsubstituted 2'-hydroxy functions. There is also no opportunity presently available for preparing arabinofuranosyl cytosines containing suitable removable protecting groups specifically at the 2'- or 3'-positions. Thus there is no way presently available to selectively acylate 1-($\beta$-D-arabinofuranosyl)-cytosines at the 3'-O-position nor is there a suitable 2'-O-protecting group available which would enable one to first selectively protect the 2'-O-position and then acylate the 3'-O-position or the 3',5'-positions. In addition it must be borne in mind that conventional acylation of cytosine nucleosides leads to acylation of both free hydroxyl functions and of the amino group on the cytosine ring. Such $N^4$-acyl derivatives of 1-($\beta$-D-arabinofuranosyl)-cytosines have been found to possess no biological activity. Accordingly, I have discovered a method of preparing 3'-O-acyl- and 3',5'-di-O-acyl- derivatives of 1-($\beta$-D-arabinofuranosyl)-cytosines by selectively cleaving the $O^2,2'$-anhydro linkage of the corresponding $O^2,2'$-anhydro-1-($\beta$-D-arabinofuranosyl)-cytosine without cleavage of the 3'-O- and/or 5'-O-acyl- groups to yield the corresponding 3'-O-acyl- or 3',5'-di-O-acyl- derivatives of 1-($\beta$-D-arabinofuranosyl)-cytosine nucleosides.

SUMMARY OF THE INVENTION

In summary the compounds of my invention can be represented by the following generic formula:

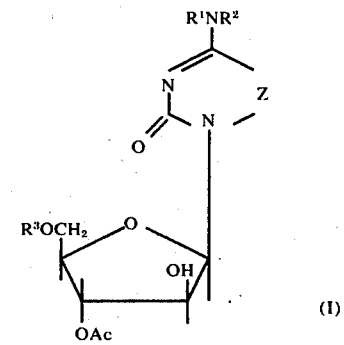

Wherein Ac is a pharmaceutically acceptable acyl group, $R^1$ and $R^2$ are independently selected from the group of hydrogen, lower alkyl, aryl, or lower alkylaryl; $R^3$ is hydrogen or a pharmaceutically acceptable acyl group; Z is the group

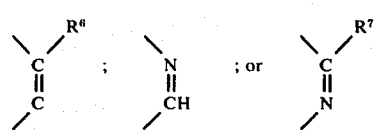

wherein $R^6$ is hydrogen, halo, lower alkyl, lower hydroxyalkyl, trifluoromethyl, azido, nitro, amino, lower alkylamino, or acylamino; and $R^7$ is hydrogen or methyl.

Also encompassed within my invention are the pharmaceutically acceptable salts of the above compounds of my invention.

In summary the process of my invention for preparing the salts of $O^2,2'$-anhydro-1-(3'-O-acyl-5'-O-acyl-$\beta$-D-arabinofuranosyl)-cytosine nucleosides comprises treating the salts of the corresponding O²,2'-anhydro-1-(β-D-arabinofuranosyl)-cytosine or 3'-O-acyl- derivatives thereof with an acyl chloride in a suitable inert organic solvent in the absence of basic proton acceptors.

In summary the process, of my invention, for selectively cleaving the O²,2'-anhydro bridge without cleavage of 3'-O-acyl- or 3',5'-di-O-acyl- groups comprises treating the corresponding 3'-O-acyl- or 3',5'-di-O-acyl- derivatives of O²,2'-1-(β-D-arabinofuranosyl)-cytosine nucleosides with a mild base under carefully controlled conditions.

The invention will be further described herein below.

FURTHER DESCRIPTION OF THE INVENTION AND PREFERRED EMBODIMENTS

The compounds of my invention can be represented by the following sub-generic formulas:

atoms, which are pharmaceutically compatible with respect to toxicity and general pharmacological properties. The term includes both saturated and unsaturated acyl groups and includes straight chain, branched chain, cycloalkyl, aromatic and heterocyclic acyl groups. The acyl group can also be optionally substituted with from 1 through 5 non-carbon substituents, preferably selected from the group of fluoro, chloro, bromo, iodo, nitro, methoxyl, alkoxycarbonyl and cyano. Suitable pharmaceutically acceptable acyl groups thus includes, for example, acetyl; butyryl; palmitoyl; octanoyl; undecenoyl; benzoyl; p-chlorobenzoyl; p-nitrophenylacetyl; phenylacetyl; behenoyl; adamantoyl; 4-methylbicyclo[2,2,2]-oct-2-enylcarbonyl; cyclopropanecarbonyl; cyclohexylacetyl; furoyl; thiophenoyl; nicotinyl; mesitoyl; acrylyl; vinylacetyl; oleyl; dichloroacetyl; trifluoroacetyl; α-bromocyclohexanecarbonyl; methoxyacetyl; β-acetoxypropionylcyanoacetyl;

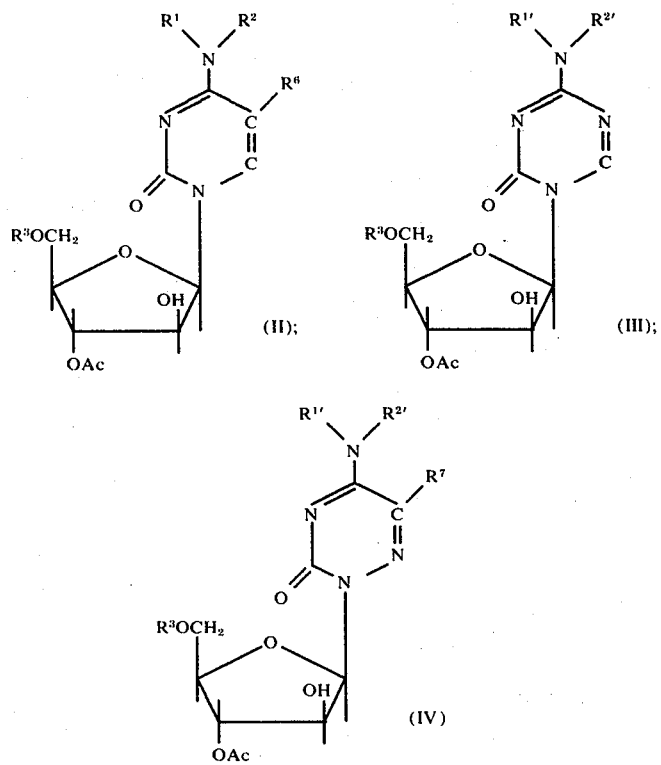

wherein Ac is a pharmaceutically acceptable acyl group having from 2 through 30 carbon atoms, $R^1$ and $R^2$ are independently selected from the group of hydrogen, lower alkyl, aryl, or lower alkylaryl, $R^{1\prime}$ and $R^{2\prime}$ are independently selected from the group of hydrogen and lower alkyl; $R^3$ is hydrogen or a pharmaceutically acceptable acyl group having from 2 through 30 carbon atoms; $R^6$ is hydrogen, halo, lower alkyl, lower hydroxyalkyl, trifluoromethyl, azido, nitro, amino, lower alkylamino, or acylamino; and $R^7$ is hydrogen or methyl.

Also included in my invention are pharmaceutically acceptable salts of the above compounds of formulas II, III and IV.

As used herein above and below the following terms have the following meanings unless expressly stated to the contrary.

The term pharmaceutically acceptable acyl groups refer to acyl groups having from 2 through 30 carbon p-nitrobenzoyl and the like.

The term lower alkyl refers to alkyl groups having about from 1 through 6 carbon atoms, and includes both straight and branched chain groups. The term lower hydroxyalkyl refers to lower alkyls having one or more hydroxy substituents. The term aryl refers to groups containing an aromatic ring such as, for example, phenyl and substituted phenyls, and having about from 6 to 20 carbon atoms. The term lower alkylaryl refers to groups having an aromatic ring containing one or more lower alkyl substituents and having a total (ring + alkyl) of 5 to 30 carbon atoms. Attachment of the alkylaryl group to the nucleoside group is via attachment through the alkyl substituent.

The term heterocyclic refers to both saturated and unsaturated heterocyclic compounds containing 1 or 2 hetero ring atoms independently selected from the group of oxygen, nitrogen and sulfur, and having about from 5 through 7 ring atoms. Typical heterocyclic groups include, for example, thienyl, pyrrolyl, furyl, pyrazolyl, thiazolyl, morpholino, piperidinyl, piperazinyl, and the like.

The term acylamino refers to the group having the formula

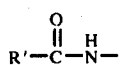

wherein R' is hydrogen, alkyl groups having from 1 through 10 carbon atoms, aryl (as defined herein above) or alkylaryl (as defined herein above). The term alkyl amino refers to the group

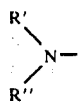

wherein one of R' or R'' is lower alkyl and the other is hydrogen or lower alkyl.

The term halo refers to the group of fluoro, chloro, bromo and iodo. Correspondingly the term halide refers to the group of fluoride, chloride, bromide and iodide.

The term pharmaceutically acceptable anion refers to anions which form hydrogen anion addition salts with the free amino group of the pyrimidine base, and which do not significantly adversely affect the pharmaceutical properties. Suitable inorganic anions include, for example, chloride, bromide, iodide, sulfate, phosphate, nitrate, sulfite and the like. Suitable organic anions include, for example, acetate, benzoate, lactate, picrate, propionate, butyrate, valerate, tartrate, maleate, fumarate, citrate, succinate, tosylate, ascorbate, palmitate, nicotinate, adipate, gluconate and the like.

All temperature ranges refer to the Centigrade scale and the term room temperature or ambient temperature refers to about 20° C.

Typical examples of the compounds of formulas II, III and IV can be had, for example, herein below by reference to Examples 5 through 12.

The preferred compounds, and pharmaceutically acceptable salts thereof, of the invention, have higher acyl substituents at the 3'-O-position and/or 5'-O-position having from 10 through 30 carbon atoms. These compounds exhibit enhanced anti-neoplastic activity. The especially preferred compounds of the invention are:

1-(3'-O-decanoyl-β-D-arabinofuranosyl)-cytosine;
1-(3'-O-myristoyl-β-D-arabinofuranosyl)-cytosine;
1-(3'-O-palmitoyl-β-D-arabinofuranosyl)-cytosine;
1-(3'-O-stearoyl-β-D-arabinofuranosyl)-cytosine;
1-(3'-O-oleoyl-β-D-arabinofuranosyl)-cytosine;
1-(3'-O-behenoyl-β-D-arabinofuranosyl)-cytosine;
1-(3'-O-arachidoyl-β-D-arabinofuranosyl)-cytosine;
1-(3'-O-cerotoyl-β-D-arabinofuranosyl)-cytosine;
1-(3'-O-chaulmoogroyl-β-D-arabinofuranosyl)-cytosine;
1-(3',5'-di-O-decanoyl-β-D-arabinofuranosyl)-cytosine;
1-(3',5'-di-O-myristoyl-β-D-arabinofuranosyl)-cytosine;
1-(3',5'-di-O-palmitoyl-β-D-arabinofuranosyl)-cytosine;
1-(3',5'-di-O-stearoyl-β-D-arabinofuranosyl)-cytosine;
1-(3',5'-di-O-oleoyl-β-D-arabinofuranosyl)-cytosine;
1-(3',5'-di-O-arachidoyl-β-D-arabinofuranosyl)-cytosine;
1-(3',5'-di-O-behenoyl-β-D-arabinofuranosyl)-cytosine;
1-(3',5'-di-O-cerotoyl-β-D-arabinofuranosyl)-cytosine; and
1-(3',5'-di-O-chaulmoogroyl-β-D-arabinofuranosyl)-cytosine.

The process, according to the invention, of preparing the salts of $O^2,2'$-anhydro-1-(3'-O-acyl-5'-O-acyl-β-D-arabinofuranosyl)-cytosine nucleosides, can be conveniently represented by the following schematic overall reaction equation:

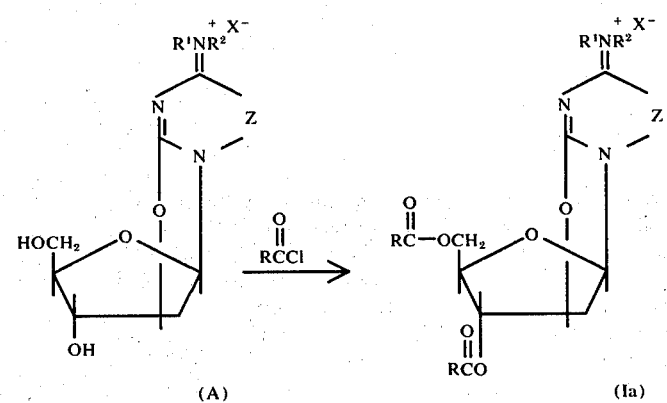

wherein the group

is a pharmaceutically acceptable acyl group having from 2 through 30 carbon atoms; $R^1$ and $R^2$ are independently selected from the group of hydrogen, lower alkyl, aryl, or lower alkylaryl; Z is the group

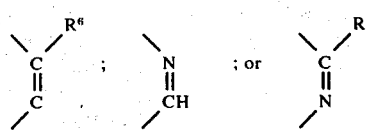

wherein $R^6$ is hydrogen, halo, lower alkyl, lower hydroxyalkyl, trifluoromethyl, zido, nitro, amino, lower alkylamino, or acylamino; and $R^7$ is hydrogen or methyl; and $X^-$ is a pharmaceutically acceptable anion.

The above process is effected by treatment of the nucleoside of formula A with a suitable acyl chloride in a suitable inert organic solvent under acidic conditions. Also as the acyl chloride will liberate hydrogen chloride, acidic conditions can be conveniently obtained by the use of acyl chloride in a neutral or acidic organic solvent. The acidic conditions ensure that the reaction is conducted in the absence of basic proton acceptors. The treatment can be conducted at temperatures in the range of about from 0° to 100° C and is typically conducted at temperatures in the range of about from 20° to 80° C. Preferably the reaction mixture is circulated and the treatment monitored, for example, by thin-layer chromatography and continued until indicated to be substantially complete. This typically requires about from 1 to 20 days depending on the particular acyl chloride used. A mole ratio of reactants in the range of about from 2 to 100 moles of acyl chloride can be used per mole of $O^2,2'$-anhydro nucleoside starting material (formula A) and preferably about from 5 to 10. Suitable acyl chlorides, which can be used include, for example, acetyl chloride, myristoyl chloride, palmitoyl chloride, stearoyl chloride, behenoyl chloride, oleoyl chloride, arachidoyl chloride, cerotoyl chloride, chaulmoogroyl chloride, adamantoyl chloride and the like. Other examples of suitable acyl chlorides can be had by reference to Wagner and Zook, *Synthetic Organic Chemistry*, Chapter 17, John Wiley & Sons (New York), 1953. Suitable inert organic solvents which can be used include, for example, dimethylacetamide, dimethylformamide, sulfolane, N-methylpyrrolidone and the like. Best results are typically obtained using dimethylacetamide. The starting materials of formula A can be prepared according to known procedures such as, for example, described in *Proc. Chem. Soc.*, 84 (1959), U.S. Pat. No. 3,463,850, or by obvious modifications of known procedures. These starting materials are conveniently prepared via a method invented by myself and A. Russell and described in a co-pending U.S. application Ser. No. 231,711 filed on even date herewith now U.S. Pat. No. 3,812,098.

The resulting 3',5'-di-O-acylated product (formula B) can be conveniently recovered via precipitation with a suitable organic solvent such as, for example, ethyl ether, ethyl acetate, benzene and the like, collected, and then further purified by recrystallization using a suitable solvent such as, for example, ethanol, acetonitrile, chloroform and the like. Also typically the longer chain 3',5'-di-O-acylated compounds remain insoluble in dimethylacetamide and can be conveniently removed by filtration and purified by recrystallization from a suitable solvent such as methanol.

Similarly, the salts of $O^2,2'$-anhydro-1-(3'-O-acyl-$\beta$-D-arabinofuranosyl)-cytosines can be acylated at the 5'-position, according to my invention, via the same procedure but preferably using about one-half the mole ratio of acyl chloride to nucleoside used in the above acylation. Also in this instance the product will contain different acyl substituents as the 3'-O-acyl- and 5'-O-position unless an acyl chloride corresponding to the 3'-O-acyl- substituent in the nucleoside starting material is used, i.e.:

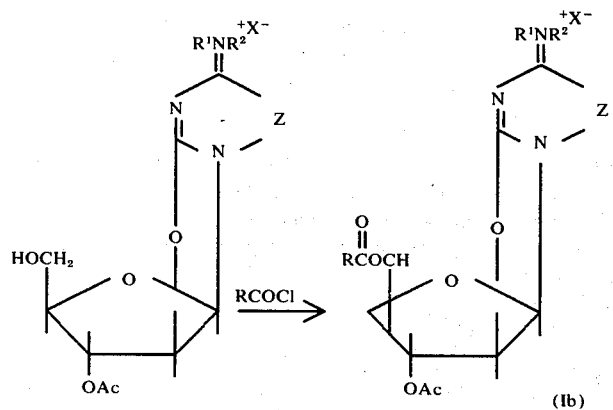

wherein Ac is a pharmaceutically acceptable acyl group; and $R^1$, $R^2$, Z, X and the group $$\underset{RC-}{\overset{O}{\underset{\|}{}}}$$

are as defined above.

The $O^2,2'$-anhydro-1-(3'-O-acyl-$\beta$-D-arabinofuranosyl)-cytosine starting materials can be prepared according to the procedure described herein below in Preparations 1, 2 and 3, and which is further described in co-pending application U.S. Ser. No. 21,206 filed Mar. 19, 1970 now U.S. Pat. No. 3,709,874 of which I am a co-inventor.

Further as can be observed in the above reaction equations, the starting materials and products have been represented as salts (i.e., $X^-$ is a pharmaceutically acceptable ion) as the parent free base, $O^2,2'$-anhydro-1-($\beta$-D-arabinofuranosyl)-cytosine nucleosides are too unstable to permit their separation and isolation.

The process of my invention for preparing the compounds of my invention comprises selectively cleaving the $O^2,2'$-anhydro bridge in the salts of $O^2,2'$-anhydro-1-($\beta$-D-arabinofuranosyl)-cytosine nucleosides, without cleaving 3'-O- or 5'-O-acyl- groups. This process can be schematically represented by the following overall reaction equation:

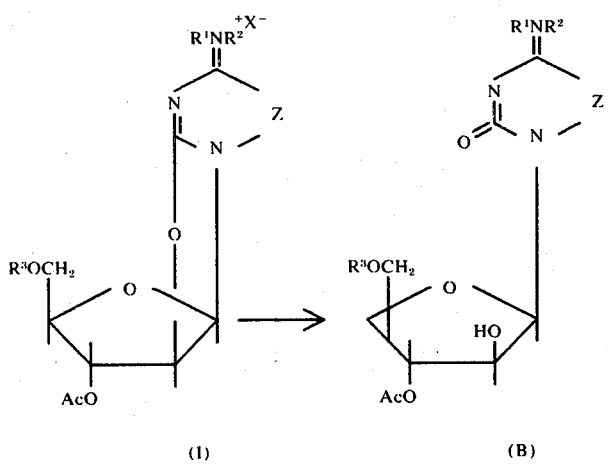

(I) → (B)

wherein $R^3$ is hydrogen or a pharmaceutically acceptable acyl group and Ac, $R^1$, $R^2$, Z and X are as defined herein above.

The above process is effected by treating the $O^2,2'$-anhydro nucleoside (formula I), in a suitable hydroxylic solvent or suitable hydroxylic solvent-organic solvent mixture with a mild base sufficient to maintain a pH in the range of about from 8 to 11. Typically the treatment is conducted at temperatures in the range of about from 0° to 100° C. Preferably the course of the reaction is carefully monitored, conveniently by UV-spectra, and the treatment discontinued as soon as formation of the cleaved product is optimized. Typically this treatment requires about from 2 to 20 hours. The resulting product can be conveniently recovered by evaporation to dryness, followed by extraction with a suitable solvent such as, for example, ethanol or partitioning between water and an organic solvent. The extracts can then be chromatographed to yield the pure product (formula B), or typically can be conveniently directly crystallized. While I have found the above separation procedure to be particularly felicitous, other suitable procedures could also be used. Suitable mild buffered bases which can be used include, for example, aqueous solutions of sodium carbonate and sodium bicarbonate; boric acid; tris-hydroxymethylamino methane and the like or by maintaining a pH of 9–10 by gradual addition of sodium hydroxide. Where a mixture of sodium bicarbonate and sodium carbonate is used, it is preferable to use temperatures in the range of about from 10° to 30° C. The term suitable hydroxylic solvent or suitable hydroxylic solvent-organic solvent refers to such solvents and solvent mixtures which do not interfere with the desired reaction. Suitable solvents which can also be used include, for example, water and aqueous solutions of dioxane, methanol, dimethylformamide, dimethylsulfoxide and the like.

The selective cleavage of the $O^2,2'$-anhydro bridge can also be effected via treatment with a hydroxylic solvent organic base combination such as, for example, aqueous pyridine or methanolic pyridine. In this instance the treatment is preferably conducted at temperatures in the range of about from 30° to 100° C for about from 2 to 24 hours. Typically, the pyridine solution will have a pyridine concentration in the range of about from 10 to 80%, wt., preferably about from 50 to 65%, by wt.

The acid addition salts of the 3'-O-acyl- and 3',5'-di-O-acyl- derivatives of 1-($\beta$-D-arabinofuranosyl)-cytosines can then be prepared via treatment (neutralization) of the parent compound with the desired acids according to conventional procedures. For example, the hydrochloride salt can be conveniently prepared via addition of a slight molar excess of methanolic hydrogen chloride to an alkanoic solution of the parent compound.

Variation in the particular salt (i.e., $X^-$) can be conveniently made by conventional ion exchange procedures.

1-$\beta$-D-Arabinofuranosyl cytosine is known to be pharmaceutically useful for its anti-viral, cytotoxic and anti-neoplastic activities. Further information concerning the pharmaceutical application of this compound can be had by reference to the literature of the art such as, for example, U.S. Pat. No. 3,462,416 (note columns 5–6 and 19–20). The pharmaceutical salts of $O^2,2'$-anhydro-1-($\beta$-D-arabinofuranosyl)-cytosines and also their 3'-O-acyl- and 3',5'-di-O-acyl- derivatives exhibit anti-viral activity and cytotoxic activity in mammals and are especially useful in the treatment of mammals infected with DNA viruses such as herpes, polyoma and vaccina. The 3'-O-acyl- and 3',5'-di-O-acyl-1-($\beta$-D-arabinofuranosyl)-cytosines and pharmaceutical salts thereof, of the invention, also exhibit anti-viral, cytotoxic and anti-neoplastic activities, and accordingly are useful in the treatment of mammals where such agents are indicated (e.g., mammals infected with DNA viral diseases such as herpes, polyoma and vaccina). I have further discovered that the compounds and pharmaceutical salts of my invention exhibit surprisingly superior anti-neoplastic activities as compared with the corresponding unacylated 1-($\beta$-D-arabinofuranosyl)-cytosine counterparts, and further that even within the compounds of my invention, the larger acyl (10 to 30 carbon atoms) derivatives have superior anti-neoplastic activities as compared with the smaller acyl derivatives. The compounds can be administered either orally or parenterally in a suitable pharmaceutical carrier. The preferred dosage will, of course, vary with the particular subject and condition being treated, but typically will be in the range of about from 50 to 500 mg./kg. of body weight.

A further understanding of my invention can be had from the following illustrative preparations and examples. Also where necessary, preparations and examples are repeated to provide sufficient starting material for subsequent examples.

PREPARATION 1

This preparation illustrates a method of preparing hydrochloride salts of $O^2,2'$-anhydro-1-(3'-O-acyl-$\beta$-D-arabinofuranosyl)-cytosine. In this example 6.6 g. of 2-acetoxy-2-methylpropionyl chloride is added to a suspension containing 2.43 g. of cytidine in 5 ml. of anhydrous acetonitrile at 80° C and stirred vigorously. After 15 minutes the mixture is cooled to room temperature and the resulting crystalline $O^2,2'$-anhydro-1-(3'-O-acetyl-$\beta$-D-arabinofuranosyl)-cytosine hydrochloride product is recovered by filtration, then washed with anhydrous acetone and dried in vacuo. The product residue is then further purified by crystallization from methanol by the slow addition of acetone.

By following the above procedure but using the corresponding cytidine derivatives, the following cyclocytidine hydrochloride salts are prepared:

$O^2,2'$-anhydro-1-(3'-acetyl-$\beta$-D-arabinofuranosyl)-$N^4$-methylcytosine hydrochloride;

$O^2,2'$-anhydro-1-(3'-O-acetyl-$\beta$-D-arabinofuranosyl)-$N^4$-dimethylcytosine hydrochloride;

$O^2,2'$-anhydro-1-(3'-O-acetyl-$\beta$-D-arabinofuranosyl)-$N^4$-phenylcytosine hydrochloride;

$O^2,2'$-anhydro-1-(3'-O-acetyl-$\beta$-D-arabinofuranosyl)-5-methylcytosine hydrochloride;

$O^2,2'$-anhydro-1-(3'-O-acetyl-$\beta$-D-arabinofuranosyl)-5-hydroxymethylcytosine hydrochloride;

$O^2,2'$-anhydro-1-(3'-O-acetyl-$\beta$-D-arabinofuranosyl)-5-fluorocytosine hydrochloride;

$O^2,2'$-anhydro-1-(3'-O-acetyl-$\beta$-D-arabinofuranosyl)-5-chlorocytosine hydrochloride;

$O^2,2'$-anhydro-1-(3'-O-acetyl-$\beta$-D-arabinofuranosyl)-5-bromocytosine hydrochloride;

$O^2,2'$-anhydro-1-(3'-O-acetyl-$\beta$-D-arabinofuranosyl)-5-iodocytosine hydrochloride;

$O^2,2'$-anhydro-1-(3'-O-acetyl-$\beta$-D-arabinofuranosyl)-5-nitrocytosine hydrochloride;

$O^2,2'$-anhydro-1-(3'-O-acetyl-$\beta$-D-arabinofuranosyl)-5-aminocytosine hydrochloride;

$O^2,2'$-anhydro-1-(3'-O-acetyl-$\beta$-D-arabinofuranosyl)-6-azacytidine hydrochloride;

$O^2,2'$-anhydro-1-(3'-O-acetyl-$\beta$-D-arabinofuranosyl)-5-methyl-6-azacytidine hydrochloride;

$O^2,2'$-anhydro-1-(3'-O-acetyl-$\beta$-D-arabinofuranosyl)-$N^4$-methyl-6-azacytidine hydrochloride;

$O^2,2'$-anhydro-1-(3'-O-acetyl-$\beta$-D-arabinofuranosyl)-$N^4$-dimethyl-6-azacytidine hydrochloride;

$O^2,2'$-anhydro-1-(3'-O-acetyl-$\beta$-D-arabinofuranosyl)-5-azacytidine hydrochloride;

$O^2,2'$-anhydro-1-(3'-O-acetyl-$\beta$-D-arabinofuranosyl)-$N^4$-methyl-5-azacytidine hydrochloride; and $O^2,2'$-anhydro-1-(3'-O-acetyl-$\beta$-D-arabinofuranosyl)-$N^4$-dimethyl-5-azacytidine hydrochloride.

By following the above procedure using 2-butyryloxy-2-methylpropionyl chloride and 2-octanoyloxy-2-methylpropionyl chloride in place of 2-acetoxy-2-methylpropionyl chloride, the corresponding 3'-O-butyryl- and 3'-O-octanoyl- derivatives of each of the above enumerated products are prepared.

PREPARATION 2

This preparation further illustrates methods of preparing $O^2,2'$-anhydro-1-(3'-O-acyl-$\beta$-D-arabinofuranosyl)-cytosine salts. In this preparation a mixture containing 100 mmoles of cytidine and 400 mmoles of 2-palmitoyloxy-2-methylpropionyl chloride in 200 ml. of acetonitrile is heated, with stirring, at 80° C for 24 hours. At the end of this time the resulting precipitate is collected by centrifugation, washed thoroughly with ethyl ether and then dried under vacuum. The resulting residue is recrystallized from methanol affording pure $O^2,2'$-anhydro-1-(3'-O-palmitoyl-$\beta$-D-arabinofuranosyl)cytosine hydrochloride. Additional product is obtained by evaporating the mother liquors to dryness, and dissolving the resulting residue in 60 ml. of methanol containing 2.55 g of acetyl chloride. The resulting solution is allowed to stand at room temperature for one hour and then evaporated to dryness affording a residue which is triturated with ethyl ether yielding a further portion of crystalline product.

Similarly by following the same procedure as above but using the corresponding cytidine derivatives as starting material, the following nucleoside hydrochloride salts are respectively prepared:

$O^2,2'$-anhydro-1-(3'-O-palmitoyl-$\beta$-D-arabinofuranosyl)-$N^4$-methylcytosine hydrochloride;

$O^2,2'$-anhydro-1-(3'-O-palmitoyl-$\beta$-D-arabinofuranosyl)-$N^4$-dimethylcytosine hydrochloride;

$O^2,2'$-anhydro-1-(3'-O-palmitoyl-$\beta$-D-arabinofuranosyl)-$N^4$-phenylcytosine hydrochloride;

$O^2,2'$-anhydro-1-(3'-O-palmitoyl-$\beta$-D-arabinofuranosyl)-5-methylcytosine hydrochloride;

$O^2,2'$-anhydro-1-(3'-O-palmitoyl-$\beta$-D-arabinofuranosyl)-5-hydroxymethylcytosine hydrochloride; $O^2,2'$-anhydro-1-(3'-O-palmitoyl-$\beta$-D-arabinofuranosyl)-5-fluorocytosine hydrochloride;

$O^2,2'$-anhydro-1-(3'-O-palmitoyl-$\beta$-D-arabinofuranosyl)-5-chlorocytosine hydrochloride;

$O^2,2'$-anhydro-1-(3'-O-palmitoyl-$\beta$-D-arabinofuranosyl)-5-bromocytosine hydrochloride;

$O^2,2'$-anhydro-1-(3'-O-palmitoyl-$\beta$-D-arabinofuranosyl)-5-iodocytosine hydrochloride;

$O^2,2'$-anhydro-1-(3'-O-palmitoyl-$\beta$-D-arabinofuranosyl)-5-nitrocytosine hydrochloride;

$O^2,2'$-anhydro-1-(3'-O-palmitoyl-$\beta$-D-arabinofuranosyl)-5-aminocytosine hydrochloride;

$O^2,2'$-anhydro-1-(3'-O-palmitoyl-$\beta$-D-arabinofuranosyl)-6-azacytidine hydrochloride;

$O^2,2'$-annydro-1-(3'-O-palmitoyl-$\beta$-D-arabinofuranosyl)-5-methyl-6-azacytidine hydrochloride;

$O^2,2'$-anhydro-1-(3'-O-palmitoyl-$\beta$-D-arabinofuranosyl)-$N^4$-methyl-6-azacytidine hydrochloride;

$O^2,2'$-anhydro-1-(3'-O-palmitoyl-$\beta$-D-arabinofuranosyl)-$N^4$-dimethyl-6-azacytidine hydrochloride;

$O^2,2'$-anhydro-1-(3'-O-palmitoyl-$\beta$-D-arabinofuranosyl)-5-azacytidine hydrochloride;

$O^2,2'$-anhydro-1-(3'-O-palmitoyl-β-D-arabinofuranosyl)-$N^4$-methyl-5-azacytidine hydrochloride; and $O^2,2'$-anhydro-1-(3'-O-palmitoyl-β-D-arabinofuranosyl)-$N^4$-dimethyl-5-azacytidine hydrochloride.

Similarly by following the above procedure but respectively using 2-octanoyloxy-2-methylpropionyl chloride; 2-undecenoyloxy-2-methylpropionyl chloride; 2-myristoyloxy-2-methylpropionyl chloride; 2-stearoyloxy-2-methylpropionyl chloride; 2-oleoyloxy-2-methylpropionyl chloride; 2-behenoyloxy-2-methylpropionyl chloride; and 2-chaulmoogroyloxy-2-methylpropionyl chloride in place of 2-palmitoyloxy-2-methylpropionyl chloride, the corresponding 3'-O-octanoyl; 3'-O-undecenoyl; 3'-O-myristoyl; 3'-O-stearoyl; 3'-O-oleoyl; 3'-O-behenoyl; and 3'-O-chaulmoogroyl derivatives of each of the above enumerated products are respectively prepared.

PREPARATION 3

This preparation further illustrates methods of preparing $O^2,2'$-anhydro-1-(3'-O-acyl-β-D-arabinofuranosyl)-cytosine salts. In this preparation a mixture containing 100 mmoles of cytidine and 400 mmoles of 2-benzoyloxy-2-methylpropionyl chloride in 200 ml. of acetonitrile is heated, with stirring, at 80° C for 24 hours. At the end of this time the resulting precipitate is collected by centrifugation, washed thoroughly with ethyl ether and then dried under vacuum. The resulting residue is recrystallized from methanol affording pure $O^2,2'$-anhydro-1-(3'-O-benzoyl-β-D-arabinofuranosyl)-cytosine hydrochloride. Additional product is obtained by evaporating the mother liquors to dryness, and the resulting residue dissolved in 60 ml. of methanol containing 2.55 g. of acetyl chloride. The resulting solution is allowed to stand at room temperature for one hour and then evaporated to dryness affording a residue which is triturated with ethyl ether yielding a further portion of crystalline product.

Similarly by following the same procedure as above but using the corresponding cytidine derivatives as starting material, the following nucleoside hydrochloride salts are respectively prepared:

$O^2,2'$-anhydro-1-(3'-O-benzoyl-β-D-arabinofuranosyl)-$N^4$-methylcytosine hydrochloride;

$O^2,2'$-anhydro-1-(3'-O-benzoyl-β-D-arabinofuranosyl)-$N^4$-dimethylcytosine hydrochloride;

$O^2,2'$-anhydro-1-(3'-O-benzoyl-β-D-arabinofuranosyl)-$N^4$-phenylcytosine hydrochloride;

$O^2,2'$-anhydro-1-(3'-O-benzoyl-β-D-arabinofuranosyl)-5methylcytosine hydrochloride;

$O^2,2'$-anhydro-1-(3'-O-benzoyl-β-D-arabinofuranosyl)-5-hydroxymethylcytosine hydrochloride;

$O^2,2'$-anhydro-1-(3'-O-benzoyl-β-D-arabinofuranosyl)-5-fluorocytosine hydrochloride;

$O^2,2'$-anhydro-1-(3'-O-benzoyl-β-D-arabinofuranosyl)-5-chlorocytosine hydrochloride;

$O^2,2'$-anhydro-1-(3'-O-benzoyl-β-D-arabinofuranosyl)-5-bromocytosine hydrochloride;

$O^2,2'$-anhydro-1-(3'-O-benzoyl-β-D-arabinofuranosyl)-5-iodocytosine hydrochloride;

$O^2,2'$-anhydro-1-(3'-O-benzoyl-β-D-arabinofuranosyl)-5-nitrocytosine hydrochloride;

$O^2,2'$-anhydro-1-(3'-O-benzoyl-β-D-arabinofuranosyl)-5-aminocytosine hydrochloride;

$O^2,2'$-anhydro-1-(3'-O-benzoyl-β-D-arabinofuranosyl)-6-azacytidine hydrochloride;

$O^2,2'$-anhydro-1-(3'-O-benzoyl-β-D-arabinofuranosyl)-5-methyl-6-azacytidine hydrochloride;

$O^2,2'$-anhydro-1-(3'-O-benzoyl-β-D-arabinofuranosyl)-$N^4$-methyl-6-azacytidine hydrochloride;

$O^2,2'$-anhydro-1-(3'-O-benzoyl-β-D-arabinofuranosyl)-$N^4$-dimethyl-6-azacytidine hydrochloride; $O^2,2'$-anhydro-1-(3'-O-benzoyl-β-D-arabinofuranosyl)-5-azacytidine hydrocloride;

$O^2,2'$-anhydro-1-(3'-O-benzoyl-β-D-arabinofuranosyl)-$N^4$-methyl-5-azacytidine hydrochloride; and $O^2,2'$-anhydro-1-(3'-O-benzoyl-β-D-arabinofuranosyl)-$N^4$-dimethyl-5-azacytidine hydrochloride.

Similarly by following the same procedure as above but using p-chlorobenzoyloxy-2-methylpropionyl chloride; and p-nitrophenylacetyloxy-2-methylpropionyl chloride in place of 2-benzoyloxy-2-methylpropionyl chloride, the corresponding 3'-O-(p-chlorobenzoyl)-; and 3'-O-(p-nitrophenylacetyl)-derivatives of each of the above enumerated products are respectively prepared.

EXAMPLE 1

This example illustrates methods according to my invention for acylating $O^2,2'$-anhydro-1-(β-D-arabinofuranosyl)-cytosines. In this example a mixture containing 1 mmole of $O^2,2'$-anhydro-1-(β-D-arabinofuranosyl)-cytosine hydrochloride and 12 mmoles of acetyl chloride in 10 ml. of dimethylacetamide is stirred at room temperature until a clear solution is observed (about 15 hours). The clear solution is then diluted with 100 ml. of ethyl ether resulting in a precipitate of crude 3',5'-di-O-acetyl-$O^2,2'$-anhydro-1-(β-D-arabinofuranosyl)-cytosine hydrochloride, which is recovered by filtration and then further purified by recrystallization from acetonitrile.

Similarly, by following the same procedure as above but using the corresponding $O^2,2'$-anhydro-1-(β-D-arabinofuranosyl)-cytosine nucleoside hydrochloride salts as starting materials, the following salts are respectively prepared:

$O^2,2'$-anhydro-1-(3',5'-di-O-acetyl-β-D-arabinofuranosyl)-5-methylcytosine hydrochloride;

$O^2,2'$-anhydro-1-(3',5'-di-O-acetyl-β-D-arabinofuranosyl)-5-fluorocytosine hydrochloride;

$O^2,2'$-anhydro-1-(3',5'-di-O-acetyl-β-D-arabinofuranosyl)-5-iodocytosine hydrochloride;

$O^2,2'$-anhydro-1-(3',5'-di-O-acetyl-β-D-arabinofuranosyl)-5-chlorocytosine hydrochloride;

$O^2,2'$-anhydro-1-(3',5'-di-O-acetyl-β-D-arabinofuranosyl)-5-acetoxymethylcytosine hydrochloride;

$O^2,2'$-anhydro-1-(3',5'-di-O-acetyl-β-D-arabinofuranosyl)-5-(α-acetoxyethyl)-cytosine hydrochloride;

$O^2,2'$-anhydro-1-(3',5'-di-O-acetyl-β-D-arabinofuranosyl)-5-trifluoromethylcytosine hydrochloride;

$O^2,2'$-anhydro-1-(3',5'-di-O-acetyl-β-D-arabinofuranosyl)-5-azidocytosine hydrochloride;

$O^2,2'$-anhydro-1-(3',5'-di-O-acetyl-$\beta$-D-arabinofuranosyl)-5-nitrocytosine hydrochloride;

$O^2,2'$-anhydro-1-(3',5'-di-O-acetyl-$\beta$-D-arabinofuranosyl)-5-acetamidocytosine hydrochloride;

$O^2,2'$-anhydro-1-(3',5'-di-O-acetyl-$\beta$-D-arabinofuranosyl)-5-methylaminocytosine hydrochloride;

$O^2,2'$-anhydro-1-(3',5'-di-O-acetyl-$\beta$-D-arabinofuranosyl)-5-azacytosine hydrochloride;

$O^2,2'$-anhydro-1-(3',5'-di-O-acetyl-$\beta$-D-arabinofuranosyl)-6-azacytosine hydrochloride;

$O^2,2'$-anhydro-1-(3',5'-di-O-acetyl-$\beta$-D-arabinofuranosyl)-$N^4$-methylcytosine hydrochloride;

$O^2,2'$-anhydro-1-(3',5'-di-O-acetyl-$\beta$-D-arabinofuranosyl)-$N^4$-phenylcytosine hydrochloride; and $O^2,2'$-anhydro-1-(3',5'-di-O-acetyl-$\beta$-D-arabinofuranosyl)-$N^4$-phenyl-5-trifluoromethylcytosine hydrochloride.

Similarly by following the same procedure as above but respectively replacing acetyl chloride with isobutyryl chloride; octanoyl chloride; benzoyl chloride; phenylacetyl chloride; p-methylbenzoyl chloride; the corresponding 3',5'-di-O-isobutyryl; 3',5'-di-O-octanoyl; 3',5'-di-O-benzoyl; 3',5'-di-O-phenylacetyl; 3',5'-di-O-(p-methylbenzoyl) hydrochloride salts of each of the above enumerated 3',5'-di-O-acetyl cytosine nucleoside salts are respectively prepared.

The above procedures are again repeated but in this instance, in place of the hydrochloride salt nucleoside starting material, the following salts are respectively used as starting material, hydroiodide, maleate, bromide, sulfate, thereby affording the corresponding 3',-5'-di-O-actyl salts. However, in this instance the product is a mixture of hydrochloride salts and the type used as nucleoside starting material.

EXAMPLE 2

This example illustrates further methods, according to the invention, of acylating the salts of $O^2,2'$-anhydro-1-($\beta$-D-arabinofuranosyl)-cytosine. In this example a suspension containing 20 mmoles of $O^2,2'$-anhydro-1-($\beta$-D-arabinofuranosyl)-cytosine hydrochloride and 200 mmoles of palmitoyl chloride in 200 ml. of dimethylacetamide is stirred at 37° C for 5 days. During this time, the reaction mixture is monitored by thin-layer chromatography, using a butanol-acetic-water (5:2:3, by vol.) solvent to ensure that the reaction is essentially complete. The mixture is then cooled to 0° C, filtered and the resulting precipitate is thoroughly washed with ethyl ether and then recrystallized from methanol yielding pure $O^2,2'$-anhydro-3',5'-di-O-palmitoyl-1-($\beta$-D-arabinofuranosyl)-cytosine hydrochloride.

Similarly by following the same procedure as above but using the corresponding $O^2,2'$-anhydro-1-($\beta$-D-arabinofuranosyl)-cytosine nucleoside hydrochloride salts as starting material, the following salts are respectively prepared:

$O^2,2'$-anhydro-5-methyl-1-(3',5'-di-O-palmitoyl-$\beta$-D-arabinofuranosyl)-cytosine hydrochloride;

$O^2,2'$-anhydro-5-fluoro-1-(3',5'-di-O-palmitoyl-$\beta$-D-arabinofuranosyl)-cytosine hydrochloride;

$O^2,2'$-anhydro-5-iodo-1-(3',5'-di-O-palmitoyl-$\beta$-D-arabinofuranosyl)-cytosine hydrochloride;

$O^2,2'$-anhydro-5-chloro-1-(3',5'-di-O-palmitoyl-$\beta$-D-arabinofuranosyl)-cytosine hydrochloride;

$O^2,2'$-anhydro-5-palmitoyloxymethyl-1-(3',5'-di-O-palmitoyl-$\beta$-D-arabinofuranosyl)-cytosine hydrochloride;

$O^2,2'$-anhydro-5-($\alpha$-palmitoyloxyethyl)-1-(3',5'-di-O-palmitoyl-$\beta$-D-arabinofuranosyl)-cytosine hydrochloride;

$O^2,2'$-anhydro-1-(3',5'-di-O-palmitoyl-$\beta$-D-arabinofuranosyl)-5-trifluoromethylcytosine hydrochloride;

$O^2,2'$-anhydro-5-azido-1-(3',5'-di-O-palmitoyl-$\beta$-D-arabinofuranosyl)-cytosine hydrochloride;

$O^2,2'$-anhydro-5-nitro-1-(3',5'-di-O-palmitoyl-$\beta$-D-arabinofuranosyl)-cytosine hydrochloride;

$O^2,2'$-anhydro-5-acetamido-1-(3',5'-di-O-palmitoyl-$\beta$-D-arabinofuranosyl)-cytosine hydrochloride;

$O^2,2'$-anhydro-5-methylamino-1-(3',5'-di-O-palmitoyl-$\beta$-D-arbinofuranosyl)-cytosine hydrochloride;

$O^2,2'$-anhydro-1-(3',5'-do-O-palmitoyl-$\beta$-D-arabinofuranosyl)-5-azacytosine hydrochloride;

$O^2,2'$-anhydro-1-(3',5'-di-O-palmitoyl-$\beta$-D-arabinofuranosyl)-6-azacytosine hydrochloride;

$O^2,2'$-anhydro-$N^4$-methyl-1-(3',5'-di-O-palmitoyl-$\beta$-D-arabinofuranosyl)-cytosine hydrochloride;

$O^2,2'$-anhydro-1-(3',5'-di-O-palmitoyl-$\beta$-D-arabinofuranosyl)-$N^4$-phenylcytosine hydrochloride; and $O^2,2'$-anhydro-1-(3',5'-di-O-palmitoyl-$\beta$-D-arabinofuranosyl)-$N^4$-phenyl-5-trifluoromethylcytosine hydrochloride.

Similarly by following the same procedure as above but respectively using myristoyl chloride, stearoyl chloride, behenoyl chloride, oleoyl chloride, chaulmoogroyl chloride, adamantoyl chloride, and 4 methylbicyclo [2,2,2]-oct-2-enylcarbonyl chloride in place of palmitoyl chloride, the corresponding 3',5'-di-O-myristoyl-; 3',5'-di-O-stearoyl-; 3',5'-di-O-behenoyl-; 3',5'-di-O-oleoyl-; 3',5'-di-O-chaulmoogroyl-; 3',5'-di-O-adamantoyl-; and 3',5'-di-O-4-methylbicyclo[2,2,2]-oct-2-enylcarbonyl- derivatives of each of the above products are respectively prepared.

EXAMPLE 3

This example illustrates methods, according to may invention, of further acylating the salts of 3'-O-acyl-$O^2,2'$-anhydro-1-($\beta$-D-arabinofuranosyl)-cytosines. In this example a mixture containing 1 mmole of 3'-O-acetyl-$O^2,2'$-anhydro-1-($\beta$-D-arabinofuranosyl)-cytosine hydrochloride and 6 mmoles of propionyl chloride in 10 ml. of dimethylacetamide is stirred at room temperature until a clear solution is observed (about 15 hours). The clear solution is then diluted with 100 ml. of ethyl ether resulting in a precipitate of crude 3'-O-acetyl-O-$^2,2'$-anhydro-5'-O-propionyl-1-($\beta$-D-arabinofuranosyl)-cytosine hydrochloride, which is recovered by filtration and then further purified by recrystallization from acetonitrile.

Similarly by following the same procedure as above but respectively using the 3'-O-acyl nucleoside products, prepared according to Preparations 1, 2 and 3 as starting material, the corresponding 3'-O-acyl-5'-O-propionyl derivatives are respectively prepared.

Similarly by following the same procedure as above, but respectively using acetyl chloride; isobutyryl chloride; octanoyl chloride; benzoyl chloride; phenylacetyl chloride; and p-methylbenzoyl chloride in place of propionyl chloride, the corresponding 3'-O-acyl-5'-acetyl-; 3'-O-acyl-5'-O-isobutyryl-; 3'-O-acyl-5'-O-octanoyl-; 3'-O-acyl-5'-O-benzoyl-; 3'-O-acyl-5'-O- phenylacetyl-; and 3'-O-acyl-5'-O-p-methylbenzoyl- derivatives of each of the above products are respectively prepared.

EXAMPLE 4

This example illustrates methods, according to may invention, of further acylating $O^2,2'$-anhydro-1-(3'-O-acyl-$\beta$D-arabinofuranosyl)-cytosine salts at the 5'-O-position. In this example a suspension containing 1 mmole of $O^2,2'$-anhydro-1-(3'-O-acetyl-$\beta$-D-arabinofuranosyl)-cytosine hydrochloride and 4 mmoles of adamantoyl chloride in 20 ml. of dimethylacetamide is stirred at room temperature for 20 days and then evaporated to dryness under vacuum. The residue is triturated several times with ethyl ether and then with ethyl acetate. The resulting material is then crystallized from a mixture of chloroform and ethyl acetate yielding pure $O^2,2'$-anhydro-1-(3'-O-acetyl-5'-O-adamantoyl-$\beta$-D-arabinofuranosyl)-cytosine hydrochloride.

Similarly by following the same procedure as above but respectively using the 3'-O-acyl nucleoside products, prepared according to Preparations 1, 2 and 3 as starting materials, the corresponding 3'-O-acyl-5'-O-adamantoyl- derivatives are respectively prepared.

Similarly by following the same procedure as above, but respectively using myristoyl chloride; stearoyl chloride; behenoyl chloride; oleoyl chloride; chaulmoogroyl chloride; palmitoyl chloride and 4-methylbicyclo[2,2,2]-oct-2-enylcarbonyl chloride in place of propionyl chloride, the corresponding 3'-O-acyl-5'-O-myristoyl-; 3'-O-acyl-5'-O-stearoyl-; 3'-O-acyl-5'-O-behenoyl-; 3'-O-acyl-5'-O-oleoyl-; 3'-O-acyl-5'-O-chaulmoogroyl; 3'-O-acyl-5'-O-palmitoyl-; and 3'-O-acyl-5'-O-4-methylbicyclo[2,2,2]-oct-2-enylcarbonyl- derivatives of each of the above products are respectively prepared.

EXAMPLE 5

This example illustrates methods, according to my invention, of preparing the 1-(3'-O-acyl-$\beta$-D-arabinofuranosyl)-cytosines. In this example a solution containing 10 mmoles of $O^2,2'$-anhydro-1-(3'-O-acetyl-$\beta$D-arabinofuranosyl)-cytosine hydrochloride, 2 g. of sodium bicarbonate and 1.5 g. of sodium bicarbonate in a mixture of 100 ml. of water and 150 ml. of dioxane, is allowed to stand at room temperature for 2 hours. The solvent is then evaporated under vacuum and the residue co-evaporated several times with ethanol. The final residue is extracted three times with 100 ml. portions of hot ethanol (about 65° C). The extracts are combined, evaporated and purified by chromatography on silicic acid using a chloroform-methanol mixture (3:1, by vol.). The product is then crystallized from acetone-ethyl acetate yielding pure 1-(3'-O-acetyl-$\beta$-D-arabinofuranosyl)-cytosine.

Similarly by following the same procedure as above but respectively using the corresponding $O^2,2'$-anhydro-1-(3'-O-acetyl-$\beta$-D-arabinofuranosyl)-cytosine products of Preparation 1 as starting material, the following compounds are respectively prepared:

1-(3'-O-acetyl-$\beta$-D-arabinofuranosyl)-$N^4$-methylcytosine;

1-(3'-O-acetyl-$\beta$-D-arabinofuranosyl)-$N^4$-dimethylcytosine;

1-(3'-O-acetyl-$\beta$-D-arabinofuranosyl)-$N^4$-phenylcytosine;

1-(3'-O-acetyl-$\beta$-D-arabinofuranosyl)-5-methylcytosine;

1-(3'-O-acetyl-$\beta$-D-arabinofuranosyl)-5-hydroxymethylcytosine;

1-(3'-O-acetyl-$\beta$-D-arabinofuranosyl)-5-fluorocytosine;

1-(3'-O-acetyl-$\beta$-D-arabinofuranosyl)-5-chlorocytosine;

1-(3'-O-acetyl-$\beta$-D-arabinofuranosyl)-5-bromocytosine;

1-(3'-O-acetyl-$\beta$-D-arabinofuranosyl)-5-iodocytosine;

1-(3'-O-acetyl-$\beta$-D-arabinofuranosyl)-5-nitrocytosine;

1-(3'-O-acetyl-$\beta$-D-arabinofuranosyl)-5-aminocytosine;

1-(3'-O-acetyl-$\beta$-D-arabinofuranosyl)-6-azacytidine;

1-(3'-O-$\beta$-D-arabinofuranosyl)-5-methyl-6-azacytidine;

1-(3'-O-acetyl-$\beta$-D-arabinofuranosyl)-$N^4$-methyl-6-azacytidine;

1-(3'-O-acetyl-$\beta$-D-arabinofuranosyl)-$N^4$-dimethyl-6-azacytidine;

1-(3'-O-acetyl-$\beta$-D-arabinofuranosyl)-5-azacytidine;

1-(3'-O-acetyl-$\beta$-D-arabinofuranosyl)-$N^4$-methyl-5-azacytidine; and 1-(3'-O-acetyl-$\beta$-D-arabinofuranosyl)-$N^4$-dimethyl-5-azacytidine.

Similarly by following the same procedure as above but using the remaining $O^2,2'$-anhydro-1-(3'-O-acyl-$\beta$-D-arabinofuranosyl)-cytosine products, prepared according to Preparation 1 as starting material, the corresponding 3'-O-acyl-1-($\beta$-D-arabinofuranosyl)-cytosine derivatives are respectively prepared.

EXAMPLE 6

This example illustrates further methods, according to my invention, of preparing 1-(3'-O-acyl-$\beta$-D-arabinofuranosyl)-cytosine compounds of the invention.

In this example a mixture of 2 g. of $O^2,2'$-anhydro-1-(3'-O-palmitoyl-$\beta$-D-arabinofuranosyl)-cytosine, 20 ml. of pyridine and 20 ml. of methanol is heated at 65° C. A clear solution results after roughly 10 minutes and heating is continued for 15 hours. The solvent is then evaporated in vacuo and the residue is partitioned between water and 1-butanol. The organic phase is further washed with water, dried, and evaporated leaving a white residue. Crystallization of this material from methanol gives pure 1-(3'-O-palmitoyl-$\beta$-D-arabinofuranosyl)-cytosine. A further portion of product is obtained by chromatography of the mother liquors on silicic acid using chloroform-methanol (4:1).

Similarly by following the same procedure but respectively using the corresponding products of Preparation 2 as starting material, the following compounds are respectively prepared:

1-(3'-O-palmitoyl-$\beta$-D-arabinofuranosyl)-$N^4$-methylcytosine;

1-(3'-O-palmitoyl-$\beta$-D-arabinofuranosyl)-$N^4$-dimethylcytosine;

1-(3'-O-palmitoyl-$\beta$-D-arabinofuranosyl)-$N^4$-phenylcytosine;

1-(3'-O-palmitoyl-$\beta$-D-arabinofuranosyl)-5-methylcytosine;

1-(3'-O-palmitoyl-$\beta$-D-arabinofuranosyl)-5-hydroxymethylcytosine;

1-(3'-O-palmitoyl-$\beta$-D-arabinofuranosyl)-5-fluorocytosine;

1-(3'-O-palmitoyl-β-D-arabinofuranosyl)-5-chlorocytosine;
1-(3'-O-palmitoyl-β-D-arabinofuranosyl)-5-bromocytosine;
1-(3'-O-palmitoyl-β-D-arabinofuranosyl)-5-iodocytosine;
1-(3'-O-palmitoyl-β-D-arabinofuranosyl)-5-nitrocytosine;
1-(3'-O-palmitoyl-β-D-arabinofuranosyl)-5-aminocytosine;
1-(3'-O-palmitoyl-β-D-arabinofuranosyl)-6-azacytidine;
1-(3'-O-palmitoyl-β-D-arabinofuranosyl)-5-methyl-6-azacytidine;
1-(3'-O-palmitoyl-β-D-arabinofuranosyl)-$N^4$-methyl-6-azacytidine;
1-(3'-O-palmitoyl-β-D-arabinofuranosyl)-$N^4$-dimethyl-6-azacytidine;
1-(3'-O-palmitoyl-β-D-arabinofuranosyl)-5-azacytidine;
1-(3'-O-palmitoyl-β-D-arabinofuranosyl)-$N^4$-methyl-5-azacytidine; and
1-(3'-O-palmitoyl-β-D-arabinofuranosyl)-$N^4$-dimethyl-5-azacytidine.

Similarly by repeating the above procedure but respectively using the remaining 3'-O-acyl- derivatives of $O^2$,2'-anhydro-1-(β-D-arabinofuranosyl)-cytosine products of Preparation 2 as starting material, the corresponding 1-(3'-O-acyl-β-D-arabinofuranosyl)-cytosines are respectively prepared.

EXAMPLE 7

This example illustrates further methods, according to my invention, of preparing 1-(3'-O-acyl-β-D-arabinofuranosyl)-cytosine compounds of the invention.

In this example a mixture of 2 g. of $O^2$,2'-anhydro-1-(3'-O-benzoyl-β-D-arabinofuranosyl)-cytosine, 20 ml. of pyridine and 20 ml. of methanol is heated at 65° C. A clear solution results after roughly 10 minutes and heating is continued for 15 hours. The solvent is then evaporated in vacuo and the residue is partitioned between water and 1-butanol. The organic phase is further washed with water, dried and evaporated leaving a white residue. Crystallization of this material from methanol gives pure 1-(3'-O-benzoyl-β-D-arabinofuranosyl)-cytosine. A further portion of product is obtained by chromatography of the mother liquors on silicic acid using chloroform-methanol (4:1).

Similarily by following the same procedure, but respectively using the corresponding products of Preparation 3 as starting material, the following compounds are respectively prepared:

1-(3'-O-benzoyl-β-D-arabinofuranosyl)-$N^4$-methylcytosine;
1-(3'-O-benzoyl-β-D-arabinofuranosyl)-$N^4$-dimethylcytosine;
1-(3'-O-benzoyl-β-D-arabinofuranosyl)-$N^4$-phenylcytosine;
1-(3'-O-benzoyl-β-D-arabinofuranosyl)-5-methylcytosine;
1-(3'-O-benzoyl-β-D-arabinofuranosyl)-5-hydroxymethylcytosine;
1-(3'-O-benzoyl-β-D-arabinofuranosyl)-5-fluorocytosine;
1-(3'-O-benzoyl-β-D-arabinofuranosyl)-5-chlorocytosine;
1-(3'-O-benzoyl-β-D-arabinofuranosyl)-5-bromocytosine;
1-(3'-O-benzoyl-β-D-arabinofuranosyl)-5-iodocytosine;
1-(3'-O-benzoyl-β-D-arabinofuranosyl)-5-nitrocytosine;
1-(3'-O-benzoyl-β-D-arabinofuranosyl)-5-aminocytosine;
1-(3'-O-benzoyl-β-D-arabinofuranosyl)-6-azacytidine;
1-(3'-O-benzoyl-β-D-arabinofuranosyl)-5-methyl-6-azacytidine;
1-(3'-O-benzoyl-β-D-arabinofuranosyl)-$N^4$-methyl-6-azacytidine;
1-(3'-O-benzoyl-β-D-arabinofuranosyl)-$N^4$-dimethyl-6-azacytidine;
1-(3'-O-benzoyl-β-D-arabinofuranosyl)-5-azacytidine;
1-(3'-benzoyl-β-D-arabinofuranosyl)-$N^4$-methyl-5-azacytidine; and
1-(3'-O-benzoyl-β-D-arabinofuranosyl)-$N^4$-dimethyl-5-azacytidine.

Similarly by repeating the above procedure but respectively using the remaining 3'-O-acyl- derivatives of $O^2$,2'-anhydro-1-(β-D-arabinofuranosyl)-cytosine products of Preparation 3 as starting material, the corresponding 1-(3'-O-acyl-β-D-arabinofuranosyl)-cytosines are respectively prepared.

EXAMPLE 8

This example illustrates methods, according to my invention, of preparing the 1-(3',5'-di-O-acyl-β-D-arabinofuranosyl)-cytosines. In this example a solution containing 10 mmoles of $O^2$,2'-anhydro-1-(3',5'-di-O-acetyl-β-D-arabinofuranosyl)-cytosine hydrochloride, 2 g. of sodium bicarbonate and 1.5 g. of sodium bicarbonate in a mixture of 100 ml. of water and 150 ml. of dioxane, is allowed to stand at room temperature for 2 hours. The solvent is then evaporated under vacuum and the residue co-evaporated several times with ethanol. The final residue is extracted three times with 100 ml. portions of hot ethanol (about 65° C). The extracts are combined, evaporated and purified by chromatography on silicic acid using a chloroform-methanol mixture (3:1, by vol.). The product is then crystallized from acetone-ethyl acetate yielding pure 1-(3',5'-di-O-acetyl-β-D-arabinofuranosyl)-cytosine.

Similarly by following the same procedure as above but respectively using the corresponding $O^2$,2'-anhydro-1-(3',5'-di-O-acetyl-β-D-arabinofuranosyl)-cytosine products of Example 1 as starting material, the following compounds are respectively prepared:

1-(3',5'-di-O-acetyl-β-D-arabinofuranosyl)-5-methylcytosine;
1-(3',5'-di-O-acetyl-β-D-arabinofuranosyl)-5-fluorocytosine;
1-(3',5'-O-acetyl-β-D-arabinofuranosyl)-5-iodocytosine;
1-(3',5'-di-O-acetyl-β-D-arabinofuranosyl)-5-chlorocytosine;
1-(3',5'-di-O-acetyl-β-D-arabinofuranosyl)-5-acetoxymethylcytosine;
1-(3',5'-di-O-acetyl-β-D-arabinofuranosyl)-5-(α-acetoxyethyl)-cytosine;
1-(3',5'-di-O-acetyl-β-D-arabinofuranosyl)-5-trifluoromethylcytosine;
1-(3',5'-di-O-acetyl-β-D-arabinofuranosyl)-5-azidocytosine;

1-(3',5'-di-O-acetyl-β-D-arabinofuranosyl)-5-nitrocytosine;

1-(3',5'-di-O-acetyl-β-D-arabinofuranosyl)-5-acetamidocytosine;

1-(3',5'-di-O-acetyl-β-D-arabinofuranosyl)-5-methylaminocytosine;

1-(3',5'-di-O-acetyl-β-D-arabinofuranosyl)-5-azacytosine;

1-(3',5'-di-O-acetyl-β-D-arabinofuranosyl)-6-azacytosine;

1-(3',5'-di-O-acetyl-β-D-arabinofuranosyl)-$N^4$-methylcytosine;

1-(3',5'-di-O-acetyl-β-D-arabinofuranosyl)-$N^4$-phenyl-cytosine; and 1-(3',5'-di-O-acetyl-β-D-arabinofuranosyl)-$N^4$-phenyl-5-trifluoromethylcytosine.

Similarly by following the same procedure as above but using the remaining $O^2$,2'-anhydro-1-(3',5'-di-O-acyl-β-D-arabinofuranosyl)-cytosine products, prepared according to Example 1 as starting material, the corresponding 3',5'-di-O-acyl-1-(β-D-arabinofuranosyl)-cytosine derivatives are respectively prepared.

EXAMPLE 9

This example illustrates further methods, according to my invention, of preparing 1-(3',5'-di-O-acyl-β-D-arabinofuranosyl)-cytosine compounds of the invention.

In this example a mixture of 2 g. of $O^2$,2'-anhydro-1-(3',5'-di-O-palmitoyl-β-D-arabinofuranosyl)-cytosine, 20 ml. of pyridine and 20 ml. of methanol is heated at 65° C. A clear solution results after roughly 10 minutes and heating is continued for 15 hours. The solvent is then evaporated in vacuo and the residue is partitioned between water and 1-butanol. The organic phase is further washed with water, dried and evaporated leaving a white residue. Crystallization of this material from methanol gives pure 1-(3',5'-di-O-palmitoyl-β-D-arabinofuranosyl)-cytosine. A further portion of product is obtained by chromatography of the mother liquors on silicic acid using chloroform-methanol (4:1).

Similarily by following the same procedure, but respectively using the corresponding products of Example 2 as starting material, the following compounds are respectively prepared:

5-methyl-1-(3',5'-di-O-palmitoyl-β-D-arabinofuranosyl)-cytosine;

5-fluoro-1-(3',5'-di-O-palmitoyl-β-D-arabinofuranosyl)-cytosine;

5-iodo-1-(3',5'-di-O-palmitoyl-β-D-arabinofuranosyl)-cytosine;

5-chloro-1-(3',5'-di-O-palmitoyl-β-D-arabinofuranosyl)-cytosine;

5-palmitoyloxymethyl-1-(3'5'di-O-palmitoyl-β-D-arabinofuranosyl)-cytosine;

5-(α-palmitoyloxyethyl)-1-(3',5'-di-O-palmitoyl-β-D-arabinofuranosyl)-cytosine;

1-(3',5'-di-O-palmitoyl-β-D-arabinofuranosyl)-5-trifluoromethylcytosine;

5-azido-1-(3',5'-di-O-palmitoyl-β-D-arabinofuranosyl)-cytosine;

5-nitro-1-(3',5'-di-O-palmitoyl-β-D-arabinofuranosyl)-cytosine;

5-acetamido-1-(3',5'-di-O-palmitoyl-β-D-arabinofuranosyl)-cytosine;

5-methylamino-1-(3',5'-di-O-palmitoyl-β-D-arabinofuranosyl)-cytosine;

1-(3',5'-di-O-palmitoyl-β-D-arabinofuranosyl)-5-azacytosine;

1-(3',5'-di-O-palmitoyl-β-D-arabinofuranosyl)-6-azacytosine;

$N^4$-methyl-1-(3',5'-di-O-palmitoyl-β-D-arabinofuranosyl)-cytosine;

1-(3',5'-di-O-palmitoyl-β-D-arabinofuranosyl)-$N^4$-phenyl-cytosine; and 1-(3',5'-di-O-palmitoyl-β-D-arabinofuranosyl)-$N^4$-phenyl-5-trifluoromethylcytosine.

Similarly by repeating the above procedure but respectively using the remaining 3',5'-di-O-acyl- derivatives of $O^2$,2'-anhydro-1-(β-D-arabinofuranosyl)-cytosine products of Example 2 as starting material, the corresponding 1-(3',5'-di-O-acyl-β-D-arabinofuranosyl)-cytosines are respectively prepared.

EXAMPLE 10

This example illustrates further methods, according to my invention, of preparing 1-(3'-O-acyl-5'-O-acyl-β-D-arabinofuranosyl)-cytosine compounds of the invention having different acyl substituents at the 3'-O- and 5'-O-positions.

In this example a mixture of 2 g. of $O^2$,2'-anhydro-1-(3'-O-acetyl-5'-O-propionyl-β-D-arabinofuranosyl)-cytosine (prepared according to Example 3), 20 ml. of pyridine and 20 ml. of methanol is heated at 65° C. A clear solution results after roughly 10 minutes and heating is continued for 15 hours. The solvent is then evaporated in vacuo and the residue is partitioned between water and 1-butanol. The organic phase is further washed with water, dried and evaporated leaving a white residue. Crystallization of this material from methanol gives pure 1-(3'-O-acetyl-5'-O-acyl-β-D-arabinofuranosyl)-cytosine. A further portion of product is obtained by chromatography of the mother liquors on silicic acid using chloroform-methanol (4:1).

Similarily by following the same procedure, but respectively using the corresponding products of Example 3 as starting material, the following compounds are respectively prepared:

1-(3'-O-acetyl-5'-O-propionyl-β-D-arabinofuranosyl)-5-methylcytosine;

1-(3'-O-acetyl-5'-O-propionyl-β-D-arabinofuranosyl)-5-fluorocytosine;

1-(3'-O-acetyl-5'-O-propionyl-β-D-arabinofuranosyl)-5-iodocytosine;

1-(3'-O-acetyl-5'-O-propionyl-β-D-arabinofuranosyl)-5-chlorocytosine;

1-(3'-O-acetyl-5'-O-propionyl-β-D-arabinofuranosyl)-5-palmitoyloxymethylcytosine;

1-(3'-O-acetyl-5'-O-propionyl-β-D-arabinofuranosyl)-5-(α-palmitoyloxyethyl)-cytosine;

1-(3'-O-acetyl-5'-O-propionyl-β-D-arabinofuranosyl)-5-trifluoromethylcytosine;

1-(3'-O-acetyl-5'-O-propionyl-β-D-arabinofuranosyl)-5-azidocytosine;

1-(3'-O-acetyl-5'-O-propionyl-β-D-arabinofuranosyl)-5-nitrocytosine;

1-(3'-O-acetyl-5'-O-propionyl-β-D-arabinofuranosyl)-5-acetamidocytosine;

1-(3'-O-acetyl-5'-O-propionyl-β-D-arabinofuranosyl)-5-methylaminocytosine;

1-(3'-O-acetyl-5'-O-propionyl-β-D-arabinofuranosyl)-5-azacytosine;

1-(3'-O-acetyl-5'-O-propionyl-β-D-arabinofuranosyl)-6-azacytosine;

1-(3'-O-acetyl-5'-O-propionyl-β-D-arabinofuranosyl)-N⁴-methylcytosine;

1-(3'-O-acetyl-5'-O-propionyl-β-D-arabinofuranosyl)-N⁴-phenylcytosine; and 1-(3'-O-acetyl-5'-O-propionyl-β-D-arabinofuranosyl)-N⁴-phenyl-5-trifluoromethyl-cytosine.

Similarly by repeating the above procedure but respectively using the remaining O²,2'-anhydro-1-(3'-O-acyl-5'-O-acyl-β-D-arabinofuranosyl)-cytosine products of Example 3 and the products of Example 4 as starting materials, the corresponding 1-(3',5'-di-O-acyl-β-D-arabinofuranosyl)-cytosines are respectively prepared.

EXAMPLE 11

This example illustrates methods of preparing the hydrochloride salts of my invention via treatment of the corresponding 3'-O- and 3',5'-di-O-acyl-1-(β-D-arabinofuranosyl)-cytosines of my invention.

In this example a solution of 5.09 g (10 mmol) of 1-(3'-O-stearoyl-β-D-arabinofuranosyl)-cytosine in warm ethanol is treated with a 10% excess (11 mmoles) methanolic hydrogen chloride. Crystallization of the resulting hydrochloride is completed by addition of ether and the resulting product is recrystallized from ethanol giving 1-(3'-O-stearoyl-β-D-arabinofuranosyl)-cytosine hydrochloride.

Similarly by following the same procedure but respectively using the products of Examples 5–10 as starting materials, the corresponding hydrochloride salt of each product is respectively prepared.

EXAMPLE 12

This example illustrates an ion exchange procedure for preparing other pharmaceutically acceptable salts of the invention. In this example a solution of 2 g. of 1-(3'-O-stearoyl-β-D-arabinofuranosyl)-cytosine hydrochloride in aqueous methanol is passed through a column containing 20 ml. of ion exchange resin in the acetate form, sold under the Trademark Dowex 50.

The effluent and washings are then evaporated to dryness and crystallized from ethanol giving 1-(3'-O-stearoyl-β-D-arabinofuranosyl)-cytosine acetate.

Similarly by following the same procedure respectively using the hydrochloride salt products of Example 11 as starting materials, the corresponding acetate salts are respectively prepared.

Obviously many modifications and variations of the invention, described herein above and below in the claims, can be made without departing from the essence and scope thereof.

What is claimed is:

1. A compound selected from the group consisting of 1-(3'-O-behenoyl-β-D-arabinofuranosyl)-cytosine; 1-(3'-O-cerotoyl-β-D-arabinofuranosyl)-cytosine; 1-(3',5'-di-O-behenoyl-β-D-arabinofuranosyl)-cytosine; 1-(3',5'-di-O-cerotoyl-β-D-arabinofuranosyl)-cytosine; and pharmaceutically acceptable salts thereof.

2. The compound of claim 1 wherein said compound is 1-(3'-O-behenoyl-β-D-arabinofuranosyl)-cytosine and pharmaceuticaly acceptable salts thereof.

3. The compound of claim 1 wherein said compound is 1-(3'-O-cerotoyl-β-D-arabinofuranosyl)-cytosine and pharmaceutically acceptable salts thereof.

4. The compound of claim 1 wherein said compound is 1-(3',5'-di-O-behenoyl-β-D-arabinofuranosyl)-cytosine and pharmaceutically acceptable salts thereof.

5. The compound of claim 1 wherein said compound is 1-(3',5'-di-O-cerotoyl-β-D-arabinofuranosyl)-cytosine and pharmaceutically acceptable salts thereof.

6. A compound selected from the group having the formula

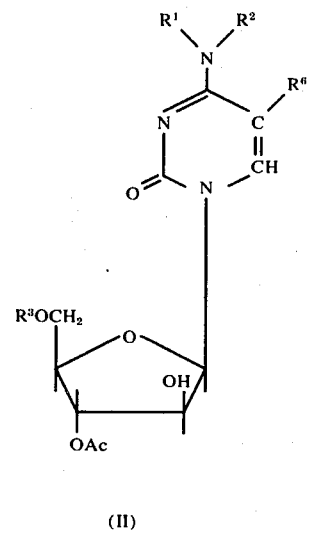

(II)

wherein Ac is a pharmaceutical acceptable acyl group having from two through 30 carbon atoms; $R^1$ and $R^2$ are each hydrogen; $R^3$ is hydrogen or a pharmaceutically acceptable acyl group having from two through 30 carbon atoms; and $R^6$ is halo; and pharmaceutically acceptable salts thereof.

7. The compound of claim 6 wherein $R^3$ is hydrogen and Ac is selected from the group consisting of acetyl, butyryl, octanoyl, palmitoyl, undecanoyl, myristoyl, stearoyl, oleoyl, behenoyl, chaulmoogroyl, benzoyl, p-chlorobenzoyl, and nitrophenylacetyl.

8. The compound of claim 7 wherein Ac is selected from the group consisting of acetyl, butyryl, octanoyl, palmitoyl, undecanoyl, myristoyl, stearoyl, oleoyl, and chaulmoogroyl.

9. The compound of claim 8 wherein said compound is selected from the group consisting of 1-(3'-O-acetyl-β-D-arabinofuranosyl)-5-fluorocytosine; 1-(3'-O-acetyl-β-D-arabinofuranosyl)-5-chlorocytosine; 1-(3'-O-acetyl-β-D-arabinofuranosyl)-5-bromocytosine; 1-(3'-O-acetyl-β-D-arabinofuranosyl)-5-iodocytosine; and pharmaceutically acceptable salts thereof.

10. The compound of claim 8 wherein said compound is selected from the group consisting of 1-(3'-O-palmitoyl-β-D-arabinofuranosyl)-5-fluorocytosine; 1-(3'-O-palmitoyl-β-D-arabinofuranosyl)-5-chlorocytosine; 1-(3'-O-palmitoyl-β-D-arabinofuranosyl)-5-bromocytosine; 1-(3'-O-palmitoyl-β-D-arabinofuranosyl)-5-iodocytosine; and pharmaceutically acceptable salts thereof.

11. The compound of claim 6 wherein $R^3$ is a pharmaceutically acceptable acyl group having from two through 30 carbon atoms.

12. The compound of claim 11 wherein said compound is selected from the group consisting of 1-(3',5'-di-O-acetyl-β-D-arabinofuranosyl)-5-fluorocytosine; 1-(3',5'-di-O-acetyl-β-D-arabinofuranosyl)-5-iodocytosine; 1-(3',5'-di-O-acetyl-β-D-arabinofuranosyl)-5-chlorocytosine; and pharmaceutically acceptable salts thereof.

13. The compound of claim 11 wherein said compound is selected from the group consisting of 1-(3',5'-di-O-palmitoyl-β-D-arabinofuranosyl)-5-fluorocytosine; 1-(3',5'-di-O-palmitoyl-β-D-arabinofuranosyl)-5-iodocytosine; 1-(3',5'-di-O-palmitoyl-β-D-arabinofuranosyl)-5-chlorocytosine; and pharmaceutically acceptable salts thereof.

* * * * *